(12) United States Patent
Ramachandran et al.

(10) Patent No.: US 9,468,206 B2
(45) Date of Patent: Oct. 18, 2016

(54) LACTOFEN AND DICAMBA DIGLYCOL AMINE LIQUID FORMULATIONS

(71) Applicant: Valent U.S.A., Corporation, Walnut Creek, CA (US)

(72) Inventors: Bhaskar M. Ramachandran, Mountain House, CA (US); Tak Wai Cheung, Mountain House, CA (US)

(73) Assignee: Valent U.S.A., Corporation, Walnut Creek, CA (US)

( * ) Notice: Subject to any disclaimer, the term of this patent is extended or adjusted under 35 U.S.C. 154(b) by 0 days.

(21) Appl. No.: 14/983,793

(22) Filed: Dec. 30, 2015

(65) Prior Publication Data
US 2016/0183518 A1 Jun. 30, 2016

Related U.S. Application Data

(60) Provisional application No. 62/098,884, filed on Dec. 31, 2014.

(51) Int. Cl.
| *A01N 37/40* | (2006.01) |
| *A01N 37/48* | (2006.01) |
| *A01N 25/22* | (2006.01) |
| *A01N 25/30* | (2006.01) |
| *A01N 25/02* | (2006.01) |
| *A01N 37/10* | (2006.01) |

(52) U.S. Cl.
CPC .............. *A01N 25/02* (2013.01); *A01N 25/22* (2013.01); *A01N 37/10* (2013.01); *A01N 37/40* (2013.01); *A01N 37/48* (2013.01)

(58) Field of Classification Search
CPC ...... A01N 25/30; A01N 25/22; A01N 37/40; A01N 37/48
See application file for complete search history.

(56) References Cited

U.S. PATENT DOCUMENTS

| 9,137,988 | B2 | 9/2015 | Zhu et al. | |
| 2008/0194408 | A1* | 8/2008 | Ramachandran | A01N 25/30 504/140 |
| 2012/0142532 | A1 | 6/2012 | Wright et al. | |
| 2014/0080706 | A1 | 3/2014 | Schnabel et al. | |
| 2014/0200139 | A1 | 7/2014 | Zhang et al. | |
| 2015/0164082 | A1 | 6/2015 | McInnes | |

OTHER PUBLICATIONS

HCAPLUS abstract 1998-606294 (1998).*
International Search Report and Written Opinion issued Mar. 17, 2016 in corresponding PCT Application No. PCT/US2015/068008.

* cited by examiner

Primary Examiner — John Pak
(74) Attorney, Agent, or Firm — Wood, Phillips, Katz, Clark & Mortimer

(57) ABSTRACT

The present invention relates to liquid agricultural formulations comprising from about 15 to about 40% w/w dicamba diglycol amine, from about 1 to about 15% w/w lactofen, from about 5 to about 40% w/w of a solvent selected from the group consisting of: (1) a solvent comprising dimethyl glutarate, dimethyl succinate, and dimethyl adipate; and (2) a solvent comprising a mixture of aromatic hydrocarbons obtained from distillation of aromatic streams derived from crude oil, from about 0.5 to about 5% w/w of a thickener with the chemical formula $(Mg,Al)_5Si_8O_{20} \times 4H_2O$, and from about 2 to about 15% w/w of a polyarylphenyl ether sulphate, ammonium salt surfactant, and methods of use thereof.

20 Claims, No Drawings

LACTOFEN AND DICAMBA DIGLYCOL AMINE LIQUID FORMULATIONS

FIELD OF THE INVENTION

The present invention generally relates to stable liquid premixture agricultural formulations comprising dicamba diglycol amine and lactofen, and methods of use thereof.

BACKGROUND OF THE INVENTION

Crop growers frequently apply herbicides, pesticides, and/or plant growth regulators ("active ingredients") in order to achieve healthier plants. The active ingredients are often mixed in a tank at or near the field and applied to the crop growing area shortly thereafter. In order to be as efficient as possible, it is desirable to apply as many of the active ingredients as possible at one time in order to minimize labor and equipment transportation costs.

Unfortunately, crop growers have been limited to certain active ingredients that can be applied simultaneously due to the physical incompatibility of many of the active ingredients. For example, many active ingredients, if mixed in a tank with water, would cause the tank mixture to separate into layers. Other combinations of active ingredients would react and form a precipitate that would fall to the bottom of the tank. Another example of incompatibility is that some combinations form a gel in the tank and therefore cannot be dispensed. In all of these examples, it is difficult to provide the crop growing area with an even distribution of the active ingredients. Uneven distribution could lead to phytotoxicity or low efficiency of the actives/waste of resources.

Dicamba diglycol amine (diglycolamine salt of 3,6-dichloro-o-anisic acid) is an herbicide that is very effective for the management of broadleaf weeds, brush and vines.

Lactofen (ethyl O-[5-(2-chloro-α,α,α-trifluoro-p-tolyloxy)-2-nitrobenzoyl]-DL-lactate) is a complex ester of acifluorfen and is a nitrophenyl ether selective herbicide. Lactofen is very effective as a post emergent weed controller.

It is desired by crop growers to apply dicamba diglycol amine and lactofen in a tank mix, however, due to their physical differences this has not been successful. Dicamba diglycol amine is water-soluble but lactofen is a solid with a low melting point and is not water-soluble. Mixing a water-soluble active ingredient with a water-insoluble active ingredient usually leads to precipitation, gelling or phase separation. Given the complexity of formulation science, it is difficult to determine which adjuvants (if any) would provide a stable formulation.

US Patent Application Publication No. 2012/0142532 is directed to stabilized herbicide solutions which contain dicamba mono ethanol amine. However, this publication fails to teach a formulation containing the more active salt, dicamba diglycol amine. Further, this publication fails to teach one of skill in the art how to produce a stable formulation which includes lactofen and dicamba diglycol amine.

US Patent Application Publication No. 2014/0080706 is broadly directed to a method of controlling undesired vegetation by preparing a tank mix having a pH of at least 7 comprising a pesticide formulation (which may include dicamba), water, a base and, optionally, an auxiliary wherein the base contains a carbonate and/or a phosphate and has a solubility in water of at least 1 g/l at 20 degrees C. This publication, however, fails to teach stable liquid premixture formulations with a pH of less than 7.

Accordingly, there is a need in the art for stable liquid premixture formulations that can include lactofen and dicamba diglycol amine. The formulations should be shelf stable and should also be able to be diluted in a tank mixer prior to application to a plant growing area.

SUMMARY OF THE INVENTION

In one aspect, the present invention is directed to liquid agricultural formulations comprising from about 15 to about 40% w/w dicamba diglycol amine, from about 1 to about 15% w/w lactofen, from about 5 to about 40% w/w of a solvent selected from the group consisting of: (1) a solvent comprising dimethyl glutarate, dimethyl succinate, and dimethyl adipate; and (2) a solvent comprising a mixture of aromatic hydrocarbons obtained from distillation of aromatic streams derived from crude oil, from about 0.5 to about 5% w/w of a thickener with the chemical formula $(Mg,Al)_5Si_8O_{20} \times 4H_2O$, and from about 2 to about 15% w/w of a polyarylphenyl ether sulphate, ammonium salt surfactant.

In another aspect, the present invention is directed to methods for using the formulations of the present invention by diluting the formulations with water, and then applying the diluted formulations to a place where a plant is growing or intended to grow.

DETAILED DESCRIPTION OF THE INVENTION

Unexpectedly, Applicant was able to prepare a stable system that allows dicamba diglycol amine and lactofen to remain in a single phase in a liquid solution. Usually at room temperature, the characteristics of dicamba diglycol amine and lactofen would make them separate into two different phases. However, Applicant was able to develop a formulation which includes specific solvents (a solvent containing dimethyl glutarate, dimethyl succinate, and dimethyl adipate or solvent containing a mixture of aromatic hydrocarbons obtained from distillation of aromatic streams derived from crude oil), a specific surfactant (polyarylphenyl ether sulphate, ammonium salt surfactant), and a specific gelling agent/thickener $((Mg,Al)_5Si_8O_{20} \times 4H_2O)$ at amounts which result in a surprisingly stable formulation. This development was unexpected because Applicant and others have attempted and failed to prepare such a formulation for a long time despite a strong need for such a product (see for example, Tables 3 and 4 below).

In one embodiment, the present invention is directed to liquid agricultural formulations comprising from about 15 to about 40% w/w dicamba diglycol amine, from about 5 to about 10% w/w lactofen, from about 5 to about 40% w/w of a solvent selected from the group consisting of: (1) a solvent comprising dimethyl glutarate, dimethyl succinate, and dimethyl adipate; and (2) a solvent comprising a mixture of aromatic hydrocarbons obtained from distillation of aromatic streams derived from crude oil, from about 0.5 to about 5% w/w of a thickener with the chemical formula $(Mg,Al)_5Si_8O_{20} \times 4H_2O$, and from about 2 to about 15% w/w of a polyarylphenyl ether sulphate, ammonium salt surfactant.

In a preferred embodiment, the formulations of the present invention comprise from about 15 to about 35% w/w dicamba diglycol amine. In a more preferred embodiment, the formulations of the present invention comprise from about 19 to about 29% w/w dicamba diglycol amine.

In another preferred embodiment, the formulations of the present invention comprise from about 2 to about 10% w/w lactofen. In a more preferred embodiment, the formulations of the present invention comprise from about 5 to about 10% w/w lactofen.

In a further preferred embodiment, the formulations of the present invention comprise from about 5 to about 20% w/w of the solvent containing dimethyl glutarate, dimethyl succinate, and dimethyl adipate. In a more preferred embodiment, the formulations of the present invention comprise from about 5 to about 15% w/w of the solvent containing dimethyl glutarate, dimethyl succinate, and dimethyl adipate. In a most preferred embodiment, the formulations of the present invention comprise about 10% w/w of the solvent containing dimethyl glutarate, dimethyl succinate, and dimethyl adipate.

In a preferred embodiment, the solvent contains from about 57 to about 67% dimethyl glutarate, from about 18 to about 28% dimethyl succinate, and from about 8 to about 22% dimethyl adipate. Rhodasolv RPDE NA (available from Rhodia) is a commercially available solvent containing 57 to 67% dimethyl glutarate, 18 to 28% dimethyl succinate, and 8 to 22% dimethyl adipate.

In an alternative embodiment, the formulations of the present invention comprise from about 5 to about 20% w/w of a solvent comprising a mixture of aromatic hydrocarbons obtained from distillation of aromatic streams derived from crude oil. In a more preferred embodiment, the formulations of the present invention comprise from about 5 to about 13% w/w of a solvent comprising a mixture of aromatic hydrocarbons obtained from distillation of aromatic streams derived from crude oil. In a most preferred embodiment, the formulations of the present invention comprise about 8% w/w of a solvent comprising a mixture of aromatic hydrocarbons obtained from distillation of aromatic streams derived from crude oil.

Aromatic 200 (available from ExxonMobil Company, i.e., Solvesso™ 200 Fluid) is an example of a commercially available solvent containing a mixture of aromatic hydrocarbons obtained from distillation of aromatic streams derived from crude oil.

In a further preferred embodiment, the formulations of the present invention comprise from about 1 to about 4% w/w of the thickener with the chemical formula $(Mg,Al)_5Si_8O_{20} \times 4H_2O$. In a more preferred embodiment, the formulations of the present invention comprise from about 2 to about 3% w/w of the thickener with the chemical formula $(Mg,Al)_5Si_8O_{20} \times 4H_2O$. In a most preferred embodiment, the formulations of the present invention comprise about 2.5% w/w of the thickener with the chemical formula $(Mg,Al)_5Si_8O_{20} \times 4H_2O$.

In yet another preferred embodiment, the formulations of the present invention comprise from about 4 to about 12% w/w of the polyarylphenyl ether sulphate, ammonium salt surfactant. In a more preferred embodiment, the formulations of the present invention comprise from about 6 to about 10% w/w of the polyarylphenyl ether sulphate, ammonium salt surfactant. In a most preferred embodiment, the formulations of the present invention comprise about 8% w/w of the polyarylphenyl ether sulphate, ammonium salt surfactant.

In yet another preferred embodiment, the formulations of the present event have a pH of less than 7. Preferably, the pH is about 6.7.

In an additional embodiment, the formulations of the present invention may include a surfactant in addition to the polyarylphenyl ether sulphate, ammonium salt surfactant. For example, a bis(2-hydroxyethyl)cocoalkylamine surfactant, an ethoxylated alkyl alcohol phosphate ester and a 5% phosphoric acid surfactant, or combinations thereof may be used in the formulation.

If an additional surfactant is included, it may be present in an amount from about 0.1 to about 3% w/w of the formulation, preferably, from about 0.8 to about 1.2% of the formulation, and more preferably, about 1.0% w/w of the formulation.

The formulations in some embodiments may also include a preservative. Examples of suitable preservatives include 1,2-benzisothiazolin-3-one based preservatives, 5-chloro-2-methyl-2H-isothiazol-3-one preservatives, and 2-methyl-2H-isothiazol-3-one preservatives. One preferred preservative is a 1,2-benzisothiazolin-3-one based preservative.

When a preservative is included in the formulations of the present invention, it is present in an amount that is preferably from about 0.01 to about 1% w/w of the formulation. More preferably, the amount is from about 0.05 to about 0.15% w/w of the formulation. In a most preferred embodiment, the amount is about 0.1% of the formulation.

In a further embodiment, the formulations of the present invention may contain an antifoam agent. In a preferred embodiment, a silicone antifoam agent may be included.

When an antifoam agent is included in the formulations of the present invention, it is preferably present in an amount from about 0.01 to about 1% w/w of the formulation. More preferably, the amount is from about 0.05 to about 0.15% w/w of the formulation. In a most preferred embodiment, the amount is about 0.1% of the formulation.

In another embodiment, the formulations of the present invention may contain phosphoric acid. When phosphoric acid is included in the formulations of the present invention, it is preferably present in an amount from about 0.001 to about 1% w/w of the formulation. More preferably, the amount is from about 0.01 to about 0.5% w/w of the formulation.

In a preferred embodiment, the weight ratio of dicamba diglycol amine to lactofen in the formulations of the present invention is from about 1:0.001 to about 1:1. In a more preferred embodiment, the weight ratio of dicamba diglycol amine to lactofen is from about 1:0.01 to about 1:0.5. In a most preferred embodiment, the weight ratio of dicamba diglycol amine to lactofen is from about 1:0.2 to about 1:0.4.

In another embodiment, the liquid agricultural formulations of the present invention comprise from about 15 to about 40% w/w dicamba diglycol amine, from about 5 to about 10% w/w lactofen, from about 5 to about 15% w/w of a solvent containing dimethyl glutarate, dimethyl succinate, and dimethyl adipate, from about 2 to about 3% w/w of a thickener with the chemical formula $(Mg,Al)_5Si_8O_{20} \times 4H_2O$, and from about 6 to about 10% w/w of a polyarylphenyl ether sulphate, ammonium salt surfactant.

In a preferred embodiment, the liquid agricultural formulations of the present invention comprise from about 24 to about 30% w/w dicamba diglycol amine, from about 8 to about 9% w/w lactofen, from about 5 to about 15% w/w of a solvent containing dimethyl glutarate, dimethyl succinate, and dimethyl adipate, from about 2 to about 3% w/w of a thickener with the chemical formula $(Mg,Al)_5Si_8O_{20} \times 4H_2O$, from about 6 to about 10% w/w of a polyarylphenyl ether sulphate, ammonium salt surfactant, a preservative, an antifoam agent, and an additional surfactant.

In a more preferred embodiment, the liquid agricultural formulations of the present invention comprise from about 24 to about 30% w/w dicamba diglycol amine, from about 8 to about 9% w/w lactofen, from about 5 to about 15% w/w of a solvent containing dimethyl glutarate, dimethyl succinate, and dimethyl adipate, from about 2 to about 3% w/w of a thickener with the chemical formula $(Mg,Al)_5Si_8O_{20} \times 4H_2O$, from about 6 to about 10% w/w of a polyarylphenyl ether sulphate, ammonium salt surfactant, from about 0.05 to about 0.15% w/w of a preservative, from about 0.05 to about 0.15% w/w of an antifoam agent, and from about 0.8 to about 1.2% w/w of an additional surfactant.

In another embodiment, the liquid agricultural formulations of the present invention comprise from about 15 to about 40% w/w dicamba diglycol amine, from about 5 to about 10% w/w lactofen, from about 5 to about 15% w/w of a solvent containing a mixture of aromatic hydrocarbons obtained from distillation of aromatic streams derived from crude oil, from about 2 to about 3% w/w of a thickener with the chemical formula $(Mg,Al)_5Si_8O_{20} \times 4H_2O$, and from about 6 to about 10% w/w of a polyarylphenyl ether sulphate, ammonium salt surfactant.

In a preferred embodiment, the liquid agricultural formulations of the present invention comprise from about 15 to about 30% w/w dicamba diglycol amine, from about 5 to about 8% w/w lactofen, from about 5 to about 15% w/w of a solvent containing a mixture of aromatic hydrocarbons obtained from distillation of aromatic streams derived from crude oil, from about 2 to about 3% w/w of a thickener with the chemical formula $(Mg,Al)_5Si_8O_{20} \times 4H_2O$, from about 6 to about 10% w/w of a polyarylphenyl ether sulphate, ammonium salt surfactant, a preservative, an antifoam agent.

In a more preferred embodiment, the liquid agricultural formulations of the present invention comprise from about 15 to about 25% w/w dicamba diglycol amine, from about 5 to about 8% w/w lactofen, from about 5 to about 15% w/w of a solvent containing a mixture of aromatic hydrocarbons obtained from distillation of aromatic streams derived from crude oil, from about 2 to about 3% w/w of a thickener with the chemical formula $(Mg,Al)_5Si_8O_{20} \times 4H_2O$, from about 6 to about 10% w/w of a polyarylphenyl ether sulphate, ammonium salt surfactant, from about 0.05 to about 0.15% w/w of a preservative, from about 0.05 to about 0.15% w/w of an antifoam agent.

In another embodiment, the present invention is directed to methods for using the formulations of the present invention by diluting the formulations with water, and then applying the diluted formulations to a place where a plant is growing or intended to grow.

As used herein, "plant" refers to at least one plant. In a preferred embodiment, the plant is an agricultural crop plant. In another preferred embodiment, the diluted formulations are applied to a field where a crop plant is growing or intended to grow. In a more preferred embodiment, the diluted formulations are applied to soybean fields.

In another embodiment, the plant is a weed. In another preferred embodiment, the diluted formulations are applied to a lawn, golf course, rights-of-way/easements (including roadways, utility, railroad, highway, pipeline, and rights-of-way that run through pasture and rangeland), utility facilities (including substations, pipelines, tankfarms, pumping stations, parking and storage areas, non-irrigation ditchbanks, and fencerows), fencerows, natural areas (including wildlife management areas, wildlife openings, wildlife habitats, recreation areas, campgrounds, trailheads and trails) and forest site preparation.

In another embodiment, the formulations are mixed with another agricultural active ingredient in a tank mixer before being applied to the place where a plant is growing or intended to grow. Examples of other agricultural active ingredients suitable for mixing with the formulations of the present invention include herbicides, pesticides and plant growth regulators.

As used herein, a "tank mixer" refers to tank where agricultural formulations are mixed with water prior to application. For example, the tank mixer may be mounted to a tractor-drawn fluid dispensing system.

Examples of suitable herbicides that may be applied with the formulation of the present invention include glyphosate salts (e.g. RoundUp® and RoundUp® PowerMax, both available from Monsanto, RoundUp is a registered trademark of Monsanto Technology LLC) and clethodim (e.g. Select Max® available from Valent U.S.A. Corporation, Select Max® is a registered trademark of Valent U.S.A. Corporation).

In yet another embodiment, when the formulations are diluted, the pH of the diluted formulation in the tank is still below 7. Preferably, the pH is about 6.7.

As used herein, all numerical values relating to amounts, weight percentages and the like, are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

The invention will be understood more clearly from the following non-limiting representative examples. Of course, the present invention is not limited to the particular embodiments and modes of operation described herein and it is possible to imagine a number of variations in the details without departing from the scope of this invention.

The examples below are presented to describe preferred embodiments and utilities of the invention and are not meant to limit the invention unless otherwise stated in the claims appended hereto.

EXAMPLES

Example 1

Preparation of Formulations 1 to 4

The dicamba diglycol amine/lactofen formulations were prepared as follows. In a vessel containing a uniform mixture of water and emulsifier, a mixture of lactofen dissolved in solvent was added under high shear. The high shear is maintained until emulsification is complete (droplet size D50=0.306 um). This emulsion was added to a premade mixture of commercially available dicamba-DGA salt solution and thickener and mixed until uniform. Finally, the co-surfactant, biocide and antifoam were added and mixed until uniform.

TABLE 1

Formulations 1 to 4

| Ingredient | % Weight of Formulations | | | |
|---|---|---|---|---|
| | Formulation 1 | Formulation 2 | Formulation 3 | Formulation 4 |
| Dicamba diglycol amine | 47.5 (27.08) | 50 (28.50) | 50 (28.50) | 53.36 (20.5) |
| Lactofen | 8.5 (8.33) | 8.5 (8.33) | 8.5 (8.33) | 6.56 (6.34) |
| Solvent containing 57 to 67% dimethyl glutarate, 18 to 28% dimethyl succinate, and 8 to 22% dimethyl adipate | 10.0 | 10.0 | 10.0 | 0 |
| Solvent containing a mixture of aromatic hydrocarbons obtained from distillation of aromatic streams derived from crude oil | 0 | 0 | 0 | 8.0 |
| $(Mg,Al)_5Si_8O_{20} \times 4H_2O$ gelling agent/thickener | 2.5 | 2.5 | 2.5 | 2.7 |
| Ethoxylated alkyl alcohol phosphate ester and 5% phosphoric acid surfactant | 1.0 | 0 | 1.0 | 0 |
| Bis(2-hydroxyethyl) cocoalkylamines surfactant | 0 | 1.0 | 0 | 0 |
| Polyarylphenyl ether sulphate, ammonium salt surfactant | 8.0 | 8.0 | 8.0 | 6.5 |
| 1,2-Benzisothiazolin-3-one based preservative | 0.1 | 0.1 | 0.1 | 0.1 |
| Silicone emulsion antifoam | 0.1 | 0.1 | 0.1 | 0.1 |
| Boron based buffer | 0.3 | 0 | 0 | 0.3 |
| Phosphoric acid | 0 | 0 | 0 | 0 to 0.5 |
| Water | q.s. | q.s. | q.s. | q.s. |
| Total | 100.0 | 100.0 | 100.0 | 100.0 |

Commercially available dicamba-DGA solutions were used as the sources of the dicamba diglycol amine in the formulations. The solution used in Formulations 1 to 3 was 57% pure and the solution used in Formulation 4 was 38.5% pure. The amounts in parentheses in the second column of Table 1 reflect the amount of dicamba. For example, Formulation 1 is 47.5% of the dicamba diglycol amine solution and the solution contained 57% dicamba diglycol amine resulting in Formulation 1 comprising 27.08% dicamba diglycol amine Lactofen, technical grade (97 to 98% purity) was used as the source of lactofen. Technical grade lactofen is available from Valent USA Corporation. The amounts in parentheses in the third column of Table 1 reflect the amount of lactofen in the formulations.

Rhodasolv RPDE NA (available from Rhodia) was used as the source of the solvent containing 57 to 67% dimethyl glutarate, 18 to 28% dimethyl succinate, and 8 to 22% dimethyl adipate.

Aromatic 200 (available from ExxonMobil Company, i.e., Solvesso™ 200 Fluid) is a solvent containing a mixture of aromatic hydrocarbons obtained from distillation of aromatic streams derived from crude oil.

Attagel® 350 (available from BASF, Attagel is a registered trademark of BASF) was used as the source of the thickener that is a medium-sized particle (average dry particle diameter of about 9 microns) gelling agent with the following chemical composition $(Mg,Al)_5Si_8O_{20} \times 4H_2O$ (a.k.a. Fuller's earth).

Phospholan™ PH-115 (available from AzkoNobel) was used as the source of the surfactant that contains ethoxylated alkyl alcohol phosphate ester and 5% phosphoric acid.

Soprophor 4D384 (available from Rhodia) was used as the source of the polyarylphenyl ether sulphate, ammonium salt surfactant.

Proxel™ (available from Lonza) was used as the source of the 1,2-benzisothiazolin-3-one based preservative. It is effective against yeast, bacteria and fungi.

Ethomeen® C12 (available from AzkoNobel, Ethomeen is a registered trademark of AzkoNobel) was used as the source of the surfactant containing bis(2-hydroxyethyl)cocoalkylamines.

Xiameter® AFE-0010 was used as the source of the silicone emulsion. It is a 10% active, food-grade silicone emulsion designed to control foam in aqueous systems.

Sodium tetraborate decahydrate was used as the source of the borate based buffer and has the following structure:

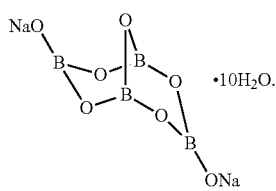

As used herein, "q.s." means that a sufficient quantity of that ingredient should be added to the formulation in order to achieve the desired weight ratios of the formulation. Determining the exact amount can be easily calculated by one of skill in the art based upon the purity of the active ingredients.

Example 2

Stability Testing of Formulation 1

Formulation 1 was subjected to numerous stability tests to determine its qualities. These studies were conducted by widely accepted methods known by those of skill in the art. Unexpectedly, Applicant found that Formulation 1 was stable and had many desirable characteristics that are described in Table 2 below.

TABLE 2

Formulation 1 Stability Test Results

| Test | Observation/Result |
| --- | --- |
| Hard Water Bloom | Excellent |
| Soft Water Bloom | Excellent |
| Redispersibility | Excellent, fully redisperses easily |
| Elevated Temperature | Excellent, no gelling or caking |
| Storage at 50 degrees Celsius for 8 weeks | Excellent, physically stable |
| Storage at 54 degrees Celsius for 2 weeks | Excellent, physically stable |

Example 3

Comparative Formulations 5 to 15

As explained above, Applicant tested numerous other thickeners and solvents which proved to be unsatisfactory. The results of these tests are summarized below in Tables 3 and 4.

TABLE 3

Comparative Formulations 5 to 12 Stability Results

| Formulation | Solvent | Result |
| --- | --- | --- |
| 5 | Butyl Carbitol™ glycol ether | Precipitate, thickens |
| 6 | Rhodiasolv Polarclean | Gels |
| 7 | Ethyl Lactate | Precipitates, gels |
| 8 | N-Methylpyrrolidone | Precipitates |
| 9 | Armid DM810 | Gels |
| 10 | Ethyl-Hexyl Lactate | Gels |

TABLE 3-continued

Comparative Formulations 5 to 12 Stability Results

| Formulation | Solvent | Result |
| --- | --- | --- |
| 11 | Jeffsol AG-1555 | Precipitates |
| 12 | Aromatic 150 | Stable |

Butyl Carbitol™ glycol ether (available from Dow) is a solvent with the chemical formula $C_4H_9(OCH_2CH_2)_2OH$.

Rhodiasolv Polarclean (available from Solvay) is a solvent which contains methyl-5-(dimethylamino)-2-methyl-5-oxopentanoate.

Ethyl Lactate (ethyl(S)-2-hydroxypropanoate, available from Sigma) is a monobasic ester that is used as a solvent.

N-Methylpyrrolidone (available from BASF Chemical Company) is a solvent that is the lactam of 4-methylaminobutyric acid.

Armid FMPC (available from AzkoNobel) is a solvent blend based on a morpholine derivative.

Armid DM810 (available from AzkoNobel) is a blend of N,N-Dimethyl Octan/Decanamide.

Ethyl-Hexyl Lactate (available from BASF, i.e., Agnique® AE 3-2EH) is a solvent with the chemical formula $C_{11}H_{22}O_3$.

Jeffsol AG-1555 (available from Huntsman) is a solvent containing propylene carbonate (1,3-Dioxolan-2-one, 4-methyl).

Aromatic 150 (available from ExxonMobil Company, i.e., Solvesso™ 150 Fluid) is a solvent containing heavy aromatic naphtha (petroleum).

TABLE 4

Formulations 13 to 15 Stability Results

| Formulation | Thickener | Result |
| --- | --- | --- |
| 13 | Kelzan ® CC | Separates |
| 14 | Kelzan ® BT | Separates |
| 15 | Natrasol ™ 250 HHX | Separates |

Kelzan® CC (available from CP Kelco, Kelzan is a registered trademark of CP Kelco) is an industrial grade xanthan gum is a high molecular weight, anionic polysaccharide produced in a pure culture fermentation process. Kelzan® CC is typically used in regular (not high salt) aqueous systems.

Kelzan® BT (available from CP Kelco, Kelzan is a registered trademark of CP Kelco) is an industrial grade xanthan gum is a high molecular weight, anionic polysaccharide produced in a pure culture fermentation process. Kelzan® BT is intended for use in high salt systems.

Natrosol™ 250 HHX (available from Ashland) is a thickener that has the following structure with an average molar substitution of 2.5 (5 ethylene oxide groups per 2 anhydroglucose units), an ultra high molecular weight, and a fine grind particle size.

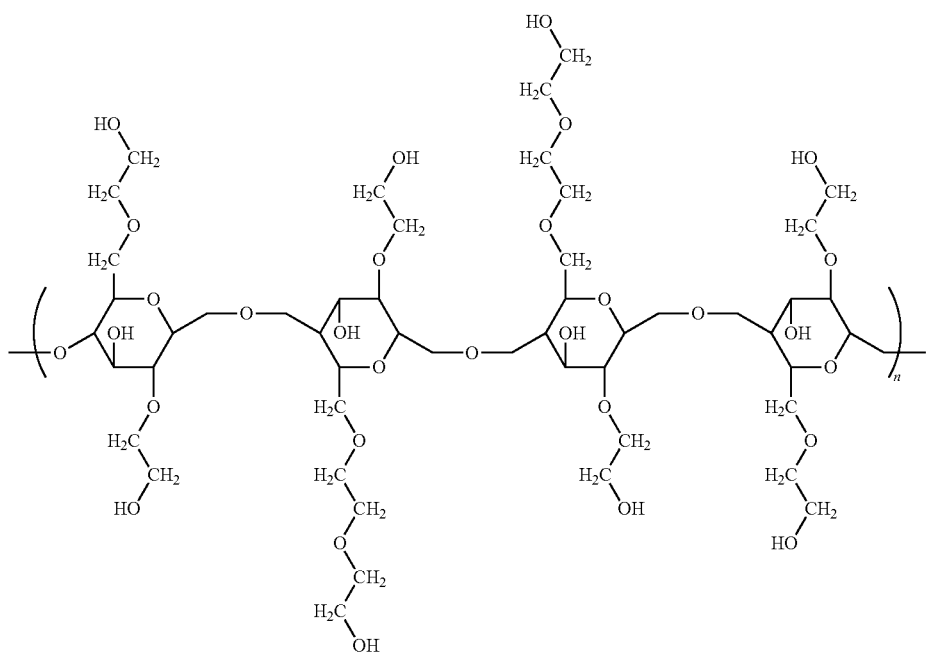

As seen in Tables 3 and 4, many other solvents and thickeners were unacceptable in the formulation. Applicant was not surprised that so many solvents and thickeners failed to provide a stable formulation because combining two actives, with very different physical properties, into a liquid formulation is very difficult. Applicant was surprised, however, when a stable formulation was eventually created.

The invention claimed is:
1. A liquid agricultural formulation comprising:
   from about 15 to about 40% w/w dicamba diglycol amine;
   from about 1 to about 15% w/w lactofen;
   from about 5 to about 40% w/w of a solvent selected from the group consisting of: (1) a solvent comprising dimethyl glutarate, dimethyl succinate, and dimethyl adipate; and (2) a solvent comprising a mixture of aromatic hydrocarbons obtained from distillation of aromatic streams derived from crude oil;
   from about 0.5 to about 5% w/w of a thickener with the chemical formula $(Mg,Al)_5Si_8O_{20} \times 4H_2O$; and
   from about 2 to about 15% w/w of a polyarylphenyl ether sulphate, ammonium salt surfactant.

2. The formulation of claim 1 comprising from about 15 to about 35% w/w dicamba diglycol amine.

3. The formulation of claim 1 comprising from about 2 to about 10% w/w lactofen.

4. The formulation of claim 1 comprising from about 5 to about 20% w/w of the solvent.

5. The formulation of claim 4 wherein the solvent comprises a mixture of aromatic hydrocarbons obtained from distillation of aromatic streams derived from crude oil.

6. The formulation of claim 1 comprising from about 1 to about 4% w/w of the thickener with the chemical formula $(Mg,Al)_5Si_8O_{20} \times 4H_2O$.

7. The formulation of claim 1 comprising from about 4 to about 12% w/w of the polyarylphenyl ether sulphate, ammonium salt surfactant.

8. The formulation of claim 1 further comprising a bis(2-hydroxyethyl)cocoalkylamine surfactant, an ethoxylated alkyl alcohol phosphate ester and 5% phosphoric acid surfactant, or combinations thereof.

9. The formulation of claim 8 comprising from about 0.1 to about 3.0% w/w of the bis(2-hydroxyethyl)cocoalkylamine surfactant, tridecanol 6EO phosphate ester and 5% phosphoric acid surfactant, or combinations thereof.

10. The formulation of claim 1 further comprising a 1,2-benzisothiazolin-3-one based preservative.

11. The formulation of claim 10 comprising from about 0.01 to about 1% w/w of the 1,2-benzisothiazolin-3-one based preservative.

12. The formulation of claim 1 further comprising a silicone antifoam agent.

13. The formulation of claim 12 comprising from about 0.01 to about 1% w/w of the silicone antifoam agent.

14. The formulation of claim 1 wherein the weight ratio of dicamba diglycol amine to lactofen is from about 1:0.001 to about 1:1.

15. The formulation of claim 14 wherein the weight ratio of dicamba diglycol amine to lactofen is from about 1:0.01 to about 1:0.05.

16. A liquid agricultural formulation comprising:
    from about 19 to about 29% w/w dicamba diglycol amine;
    from about 5 to about 10% w/w lactofen;
    from about 5 to about 15% w/w of a solvent containing dimethyl glutarate, dimethyl succinate, and dimethyl adipate;
    from about 2 to about 3% w/w of a thickener with the chemical formula $(Mg,Al)_5Si_8O_{20} \times 4H_2O$; and
    from about 6 to about 10% w/w of a polyarylphenyl ether sulphate, ammonium salt surfactant.

17. The formulation of claim 16 further comprising a preservative, an antifoam agent, and an additional surfactant.

18. The formulation of claim 17 comprising from about 0.05 to about 0.15% w/w of the preservative, from about 0.05 to about 0.15% w/w of the antifoam agent, and from about 0.8 to about 1.2% w/w of the additional surfactant.

19. A method for protecting plants comprising diluting the formulation of claim 1 with water, and applying the diluted formulation to a place where a plant is growing or intended to grow.

20. The method of claim 19 comprising diluting the formulation of claim 1 in a tank mixer, adding other active ingredients to the tank mixer, and applying the tank mixture to the place where a plant is growing or intended to grow.

* * * * *